(12) United States Patent
Mollstam et al.

(10) Patent No.: US 8,746,547 B2
(45) Date of Patent: Jun. 10, 2014

(54) MEDICAL INDICATION DEVICE AND IDENTIFICATION METHOD

(75) Inventors: Anders Mollstam, Saltsjö (SE); Sven Milton, Vikingstad (SE)

(73) Assignee: Medical Vision Research and Development AB, Nacka (SE)

(*) Notice: Subject to any disclaimer, the term of this patent is extended or adjusted under 35 U.S.C. 154(b) by 0 days.

(21) Appl. No.: 12/657,458

(22) Filed: Jan. 21, 2010

(65) Prior Publication Data

US 2010/0155465 A1 Jun. 24, 2010

Related U.S. Application Data

(63) Continuation-in-part of application No. 10/530,409, filed as application No. PCT/SE03/01574 on Oct. 9, 2003, now Pat. No. 7,661,582.

(51) Int. Cl.
*G06F 17/00* (2006.01)

(52) U.S. Cl.
USPC .. 235/375; 235/451; 235/462.01; 235/462.13

(58) Field of Classification Search
USPC ............ 235/375, 376, 439, 451, 454, 462.01, 235/462.13, 462.14, 462.43, 485, 486, 492
See application file for complete search history.

(56) References Cited

U.S. PATENT DOCUMENTS

| | | | |
|---|---|---|---|
| 4,249,163 A * | 2/1981 | Maurer et al. ................ 235/379 |
| 4,347,499 A * | 8/1982 | Burkman et al. ........ 340/815.69 |
| 5,131,823 A | 7/1992 | Guignard |
| 5,400,267 A | 3/1995 | Denen et al. |
| 5,431,627 A * | 7/1995 | Pastrone et al. ................ 604/65 |
| 5,460,490 A | 10/1995 | Carr et al. |
| 5,591,344 A * | 1/1997 | Kenley et al. ................ 210/636 |
| 5,740,140 A * | 4/1998 | Arataki et al. ............. 369/53.45 |
| 5,810,770 A | 9/1998 | Chin et al. |
| 6,092,190 A * | 7/2000 | Lee .................................. 713/2 |
| 6,106,498 A | 8/2000 | Friedli et al. |
| 6,490,491 B1 * | 12/2002 | Hartmann et al. .............. 700/86 |
| 6,626,355 B2 * | 9/2003 | Sasse et al. .................... 235/375 |
| 6,802,659 B2 * | 10/2004 | Cremon et al. ................. 400/76 |

(Continued)

FOREIGN PATENT DOCUMENTS

| | | |
|---|---|---|
| EP | 1 787 606 B1 | 8/2008 |
| WO | WO 2006/036600 | 4/2006 |

OTHER PUBLICATIONS

DCT, Informatics Kajang, (2000) Hand Out 4: Supplementary Notes 4, Microprocessor & Random Access Memory, pp. 1-4.*

*Primary Examiner* — Paultep Savusdiphol
(74) *Attorney, Agent, or Firm* — Renner, Otto, Boisselle & Sklar, LLP.

(57) ABSTRACT

A medical-technical identification device for identifying a sterile product and a method of identifying such a product are provided. The product may be intended for one-time-use only, when connected to a piece of medical equipment. A fixedly mounted information carrier is adapted to deliver or to offer specific product information in a contactless fashion to a reading element connected to the medical equipment. The function of the identification device is improved so that even specific data can be forwarded to the medical equipment such as an infusion-type fluid pump. Thus operation of the pump may be reprogrammed, for example, to change the calibration factor or the operation mode or to change irrigation depending on the patient group to undergo surgery.

19 Claims, 4 Drawing Sheets

(56) References Cited

U.S. PATENT DOCUMENTS

| | | |
|---|---|---|
| 7,108,184 B2 * | 9/2006 | Mase et al. ............... 235/462.01 |
| 2001/0020148 A1 * | 9/2001 | Sasse et al. .................... 604/65 |
| 2001/0022166 A1 * | 9/2001 | Yamaguchi et al. ....... 123/179.3 |
| 2002/0188259 A1 * | 12/2002 | Hickle et al. ................. 604/189 |
| 2002/0191998 A1 * | 12/2002 | Cremon et al. ................. 400/76 |
| 2003/0088290 A1 * | 5/2003 | Spinelli et al. ................. 607/30 |
| 2004/0127807 A1 * | 7/2004 | Hatlesad et al. .............. 600/529 |
| 2006/0058804 A1 | 3/2006 | Mollstam |
| 2006/0187080 A1 * | 8/2006 | Slatter ..................... 340/825.22 |

* cited by examiner

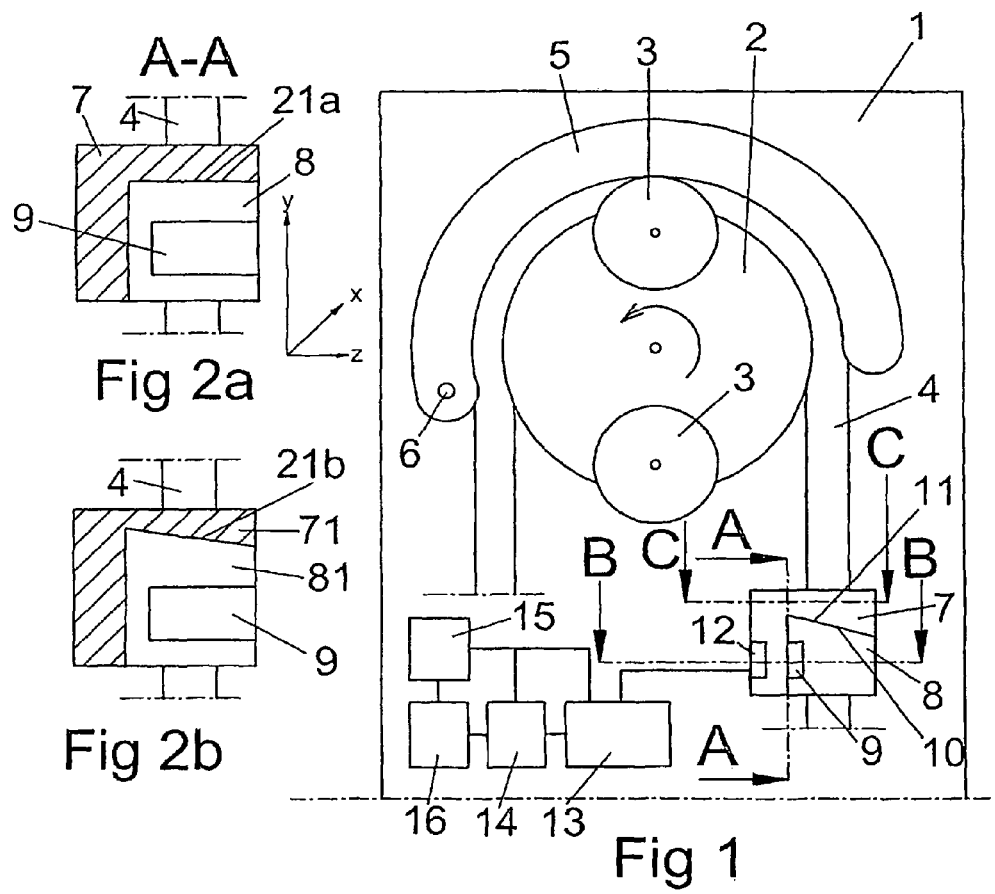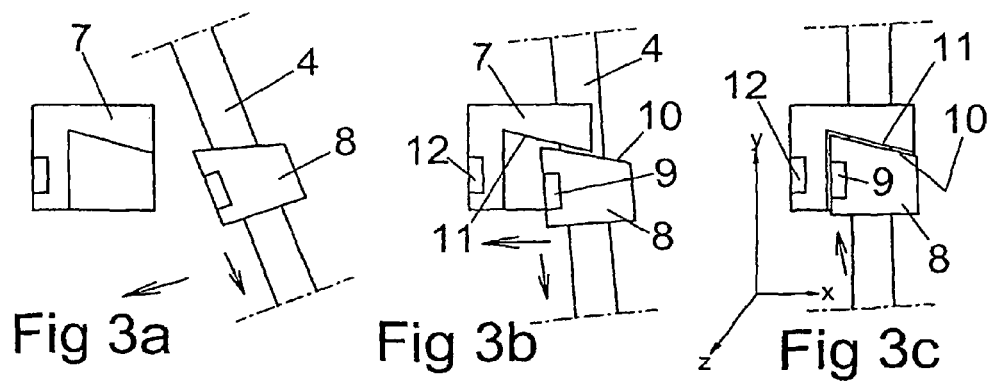

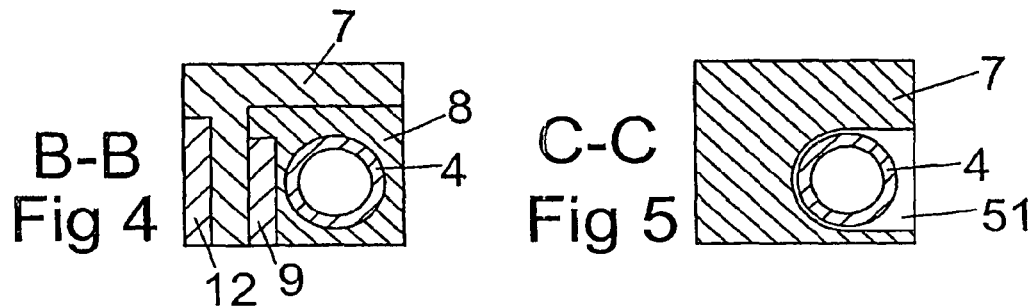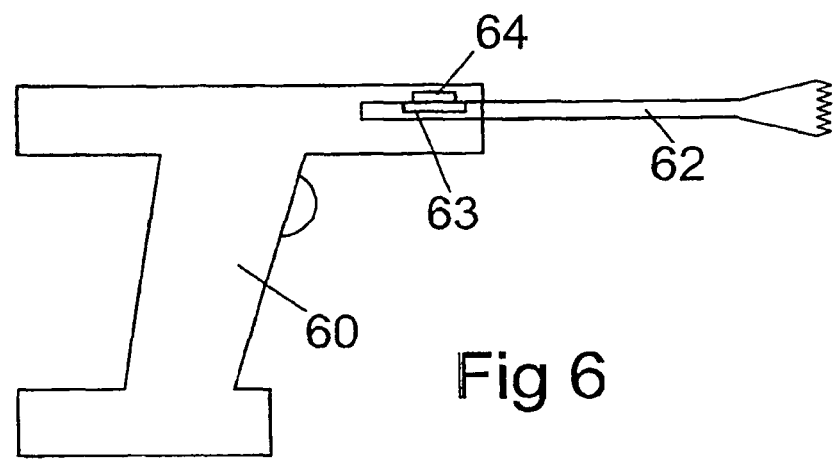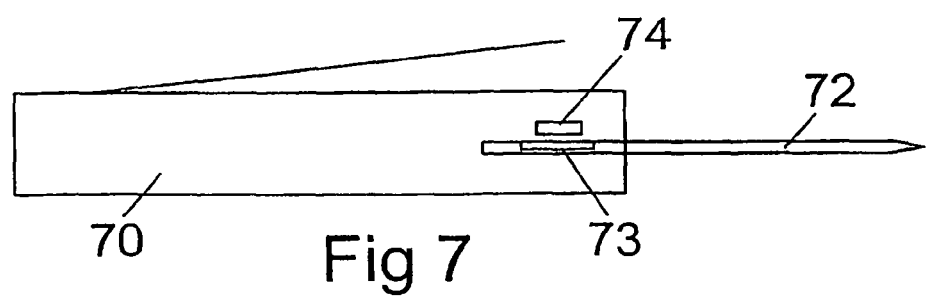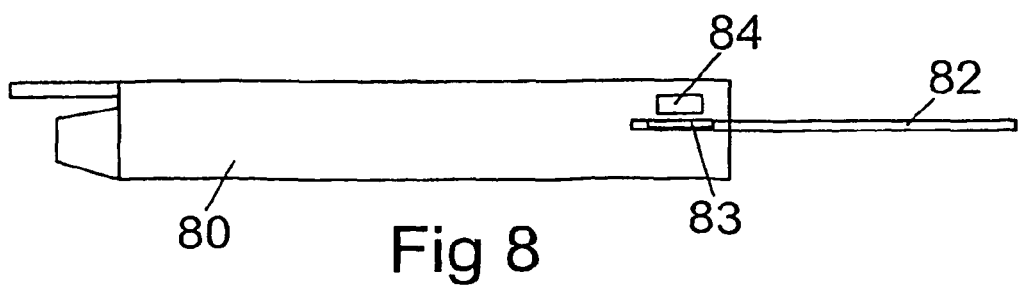

MEDICAL INDICATION DEVICE AND IDENTIFICATION METHOD

CROSS-REFERENCE TO RELATED APPLICATIONS

This application is a continuation-in-part of application Ser. No. 10/530,409 filed Aug. 2, 2005, now U.S. Pat. No. 7,661,582, which claims priority from PCT/SE2003/001574, filed Oct. 9, 2003.

BACKGROUND OF THE INVENTION

1. Field of the Invention

The identification device pertains to the medical field and then particularly to the field in which sterile products shall be connected together and in which it is of paramount importance that the correct parts are connected, for instance when part of a hose shall be connected to an infusion-type fluid pump. It also includes methods and products to transfer data and software between the part and for example the pump.

2. Description of the Related Art

U.S. Pat. No. 5,131,823 makes known a device for joining a connection piece to peristaltic pump. As evident from the descriptive part of the document, one end of a hose is provided with a sleeve for connection to an end of a further hose. The connection sleeve includes a disc-shaped angled collar, which is intended to be received in a slot disposed in a support device and facing towards the disc. The sleeve together with its angled disc functions to fix the hose ends in a correct position relative to the peristaltic pump. Moreover, the angled disc causes an increase in tension forces caused by the pump to result in a self-locking action by virtue of the sleeve being pressed against a seat.

One problem with this device is that hoses can be mixed-up, even when color-marked. Furthermore, unintentional confusion between the hoses can go as far as causing the equipment to be used wrongly in the absence of any indication to the contrary.

Sasse et al. in U.S. Pat. No. 6,626,355 disclose a medical device comprising a medical apparatus e.g. a hose cassette for a peristaltic pump, comprising an accessory port including a storage unit wherein coded identification information is stored, wherein only authorized manufacturers will receive a proprietary key for de-coding it. Their aim is to stop the supply of accessory pieces not meeting technical or medical requirements and to stop people from inadmissibly re-using the accessory pieces. Their invention relies on the use of proprietary codes and on the medical device being activated by means of the information stored in an information device. In the invention herein, the function of the identification device also works to identify the correct accessory piece but through giving advice at a display on the medical apparatus, and has been improved so that it also allows specific data related to the equipment to be forwarded to it independent of the features of the identification device. Thus, for example operation of the medical equipment can be re-programmed on request from e.g. manufacturers, medical or technical staff. This is further explained below.

In this respect there are several patent and patent applications disclosing control of medical equipment depending on the information included in the medical device attached to it. However, in no case is the information related to or specific to the calibration, re-programming or the use of the medical equipment itself.

Chin et al. in U.S. Pat. No. 5,810,770 discloses a pump assembly wherein a tube set cassette is provided with a ROM containing basic data identifying the type of tube set included into a peristaltic pump. This is used to determine if the tube set was previously used.

Malackowski in WO 2006/036600 goes a bit further. Data associated with the length and diameter of the tube are used to determine how long the pump should be run. In some aspects of his invention the data can be used to regulate priming of the tube and the irrigation device, as well as to regulate speed of the motor/pump head.

U.S. Pat. No. 5,400,267 teaches that a non-volatile memory may be pre-programmed to store utilization limits and parametric data for the equipment. The equipment is disabled if a utilization limit is exceeded. The parametric data is also used to regulate the power supplied to the equipment.

Carr et al. in U.S. Pat. No. 5,460,490 discloses an irrigation/aspiration pump system capable of operating in a plurality of different modes suitable for a variety of different endoscopic surgical procedures. The pump system operates with a selected one of a plurality of tubing sets, each tubing set being adapted to provide irrigation and aspiration for a particular surgical procedure and coded to define the type of procedure for which the tubing set is designed. The code associated with the tubing cassette assures that the parameters, with which the system will be operating, when the chosen tubing set is being used, are those for which the tubing set is designed.

More recently EP 1787606 provides a surgical system and a cassette containing unique information for identifying performance characteristics specific to the cassette. Cassette information that may be encoded includes features such as aspiration/irrigation pressure sensor, calibration data, peristaltic pump flow data, and any other data captured during testing of the cassette during manufacture. Although the information provided in the cassette may affect operation of the surgical system, it is not specific to the pump or medical equipment but to the cassette itself.

Pastrone et al. in U.S. Pat. No. 5,431,627 and Friedli et al. in U.S. Pat. No. 6,106,498 disclose similar systems in which optical/non optical identification means are utilized to determine the correct performance characteristics required by a pump for a particular cassette. Detectors in the pump detect identification means on the cassette body. Thus, the pump is able to automatically determine which cassette has been installed and to adjust certain parameters to match de cassette.

Neither of the cited references discloses an identification device also allowing re-programming and control of the medical device operation independent of the features of the attached device itself. According an embodiment of the invention herein, the identification device may contain both information related to the device itself and information concerning the medical equipment, the information being used in all cases for regulating the medical equipment functions and operation.

The parent application of this application does neither disclose an identification device also allowing re-programming and control of the medical device operation independent of the features of the attached device itself.

SUMMARY OF THE INVENTION

The present invention relates to an identification device and a method of identifying a sterile product, for example a product intended for one-time-use only, when connected to a piece of medical equipment, wherein the sterile product includes a fixedly mounted information carrier, which is adapted to deliver or to offer specific product information in a contact-less fashion to a reading element connected to the equipment.

An object of the present invention is to identify that the correct coupling elements have been joined together, and to prevent a piece of equipment from functioning when coupling the wrong product to the equipment, and to record a product history. This avoids connection of products intended for one-time use only to the equipment, when e.g. this product has been withdrawn/stopped by the manufacturer or has passed its expiry date with respect to its sterility.

The identification device of the present invention can be used by a processor-controlled storage unit and a control unit for controlling the medical equipment in response to information obtained from the hose or cassette. Examples how this can be made is for example found below or in US2007249993.

Identification is achieved through the medium of an information carrier connected to the hose or cassette and programmed with relevant information, such as approved use, lot number, batch number, hose dimensions, elasticity, and manufacturer, all of this information being programmed in the information carrier either in connection with or subsequent to manufacture.

Another object of the invention herein is to make sure that technical data related to operation of equipment can be forwarded from the manufacturer to the distributed equipments through the use of the information carrier on the hose or cassette. This data includes operation modes, calibration factors, leasing or service expiration date, as well as data related to specific patient groups, surgical procedure, final user preferred operation settings, etc.

There has thus been outlined, rather broadly, the more important features of the invention in order that the detailed description thereof may be better understood, and in order that the present contribution to the art may be better appreciated. There are additional features of the invention that will be described hereinafter.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

The invention will now be described in more detail with reference to exemplifying embodiments thereof and also with reference to the accompanying drawings.

FIG. 1 illustrates an embodiment of an inventive identification device.

FIG. 2*a* is a sectional view of a first embodiment of the inventive device shown in FIG. 1, the view being taken on the line A-A in FIG. 1.

FIG. 2*b* is a sectional view of a second embodiment of the invention according to FIG. 1 taken on the line A-A.

FIGS. 3*a-c* illustrates a sequence of manual operations undertaken in securing a hose in accordance with the invention.

FIG. 4 is a sectional view taken on the line B-B in FIG. 1.

FIG. 5 is a sectional view taken on the line C-C in FIG. 1.

FIG. 6 is a schematic view of an oscillating saw in accordance with the invention.

FIG. 7 is a schematic view of a drill in accordance with the invention.

FIG. 8 is a schematic view of a shaver in accordance with the invention.

DETAILED DESCRIPTION OF THE INVENTION AND PREFERRED EMBODIMENTS THEREOF

Figure 9:
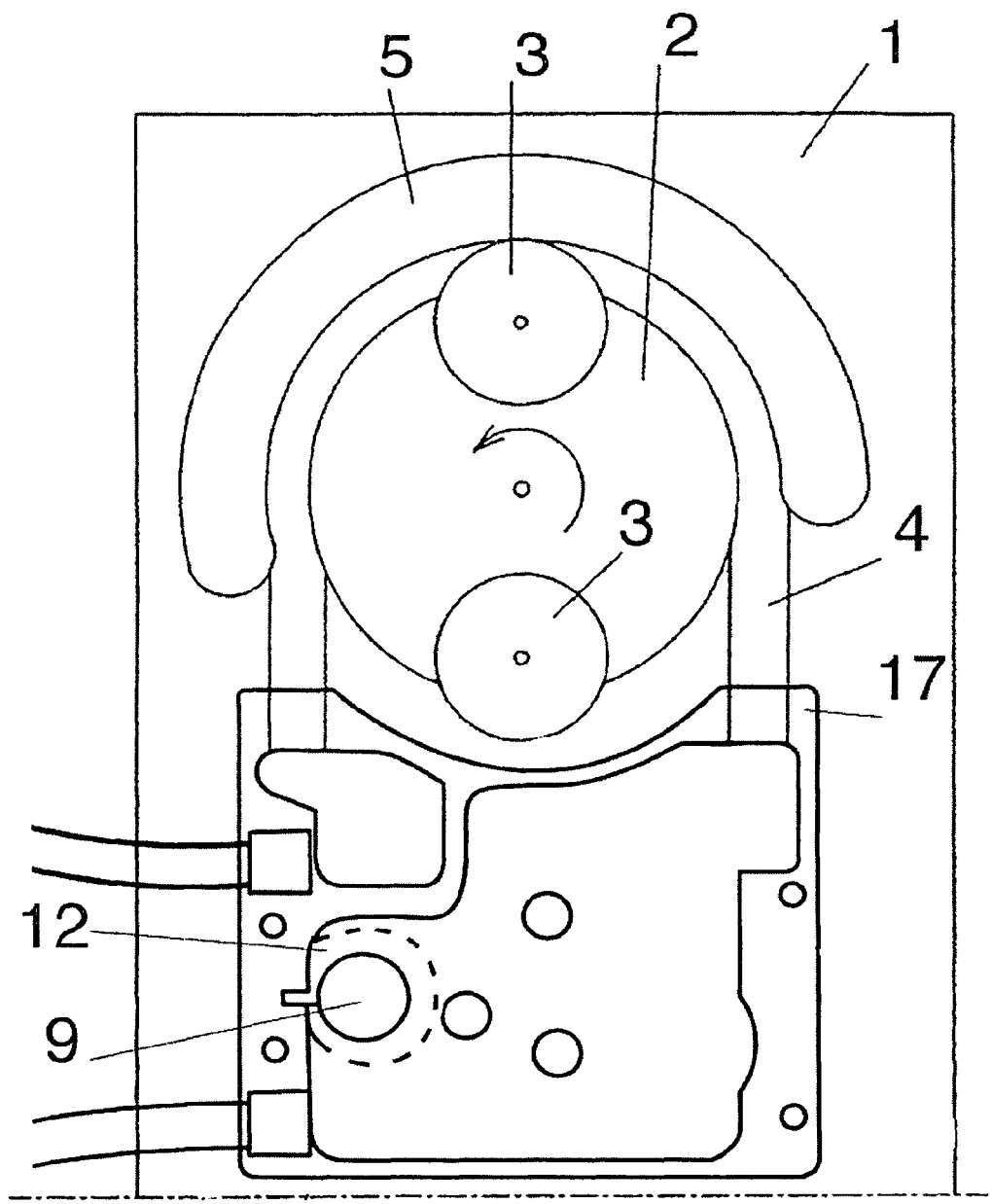
FIG. 9 illustrates another embodiment of a device with a hose in combination with a cassette design.

According to the first embodiment, the identification device of the invention herein is used to ensure the correct connection of a sterile product to a piece of medical equipment and/or that the correct product has been connected, for instance that a hose or cassette is of the correct type for the use given, and to indicate the number of times that the sterile product has been used and therewith signal for service, stoppage or replacement of equipment.

The invention relates to a method of identifying a sterile product and a medical-technical identification device for identifying the sterile products, e.g. products intended for one-time-use only, when connected to medical equipment. The sterile product has fixedly attached thereto an information carrier which is adapted to deliver specific product information to a reading element connected to the equipment or to provide the reading element with such information, in a contactless fashion. The information carrier is a passive component attached to the hose or cassette and may therewith have the nature of a RFID chip, smart card, memory card or other semiconductor memory The sterile product may particularly consist of an elastic hose part with or without a cassette part. In the case of one embodiment, the information carrier is mounted in a holder and the reading element is mounted in a fixation seat. The exchange of information between the information carrier and the reading element does not take place until the hose part has been fully connected to the medical equipment. In another embodiment, the information carrier and the reading element are adapted to take a fixed position relative to one another when the hose part is connected actively to the equipment. In one specific embodiment the holder of the information carrier includes a planar slide surface that defines an angle in accordance with the aforesaid, such that the normal to the slide surface will not extend parallel to the symmetry axis of the hose part and such that the slide surface will fit with a correspondingly orientated slide surface in the fixation seat. In one embodiment both slide surfaces are directed so that a force applied to press the surfaces against each other causes the information carrier and the reading element to be brought into mutual alignment in the X-direction and the Y-direction. In one embodiment the two slide surfaces are directed so that the information carrier and the reading element will also be brought into alignment in the Z-direction.

The reading element is connected to a registering unit which in turn, is connected to both a storage unit and to an analyzing unit. The analyzing unit sends signals to a control unit, which is adapted to bring influence to bear on the medical equipment. The arrangement also includes a presentation unit, which functions to show information from both the analyzing unit and the storage unit. Also included is a programming unit, which is connected to the analyzing unit, control unit or storage unit.

The transfer of information between the information carrier and the reading element is effected through the medium of one or more of the following devices: bar code, Blue-tooth™, radio waves, light waves—e.g. infrared light, electromagnetism, radioactivity, or chemical transmission as known in the art.

Once the equipment has used the sterile product, data indicating such use is transferred from the equipment to the information carrier. The information on the information carrier is thus changed. If the sterile device is later attached to a medical device, the information will influence the control of the medical equipment.

In another embodiment the information carrier and the reading element are adapted to take a fixed position relative to one another when the cassette part is connected actively to the medical equipment. The holder of the information carrier is integral to the cassette part and will fit with a correspondingly orientated surface of the medical equipment.

An identification check is carried out with the aid of the information carrier mounted in the sterile medical article, e.g. an article intended for one-time-use only, and containing unique identification information which is read by a reading element mounted in a medical apparatus. The information is registered in the device and can then be used in respect of the following procedures, among other things:

1. The receiver ascertains whether or not the article coupled to the medical apparatus has been approved. The apparatus may be programmed to shut down if the article is found not to be approved, therewith avoiding an accident. An example of a non-approved article may be that:

the article has been stopped, for instance its batch number/lot number has been withdrawn by the manufacturer,
the article has passed its sterility date
the article is about to be reused. The article can be allowed to be connected to an apparatus several times, although within a limited time period, e.g. within a 24 hour period.

2. Stored as a file document, e.g. on the hard disk of a computer. This stored information can then be retrieved to:

show for how long articles have been connected to the apparatus.
show how often the apparatus has been used, for instance how often the article has been connected up during a given time interval. The information can be used to inform the user of the extent to which the apparatus has been in use, i.e. to optimize the degree of use, to inform the user when it is appropriate to send the apparatus away for service.

For achieving this second object of this invention an alternative version of the identification device of the type mentioned above has been designed, which is one feature of this new invention. According to this embodiment, technical data can be forwarded from the manufacturer to the distributed medical equipment, i.e. in those cases where the manufacturer wishes to change a calibration factor in all equipments sold. In the serial production of the disposable products, the data "key" for "New calibration factor" is entered, and the new numerical value of it. Thus, minor updates can be made without the call for technical staff. This refers to calibration values that are not immediately obvious to the user, as the operating mode(s) is the same. Thus performance is improved as a result of a small update. Data of time and date might also be entered to determine if a lease or service period has expired.

In another example the medical identification device can receive data regarding operation mode and the medical equipment can be programmed to:

Service mode: The identification device can be specially designed to allow service, maintenance and calibration of the medical equipment (pump) by authorized service engineers. The identification device would have connectors for pressure gauges for calibration of the pump, and adaptors for flow detectors, "joints" with calibrated compliance values and other components for system maintenance. Cassettes for service of the system would have data on the RFID tag to specifically indicate that cassettes for service are attached to the pump.

Demo mode: An identification device can be assigned a non-medical or special use. The specific use is coded in the RFID tag, and can for instance be that the medical equipment or pump is in a demonstration mode for sales exhibitions or user training. Such operating mode of the pump can allow for automatic variations in flow settings for demonstration purposes. The identification device would be connected as a loop with a simulated joint for illustration.

These two modes refer to operation modes of the pump that would expose danger to a patient if entered by mistake. This is a critical safety problem that has a solution by enabling those different operating modes only by the use of dedicated cassettes that are designed for these respective purposes.

User operation mode: A cassette can carry data on the RFID tag that enables a user specific operating mode. For instance, a cassette can be designed to order for operating a parameter set that is preferred by a specific user. If a surgeon has specific set up preferences in selection of pressure values, flow values, blood and debris detection sensitivity and functional features selected on or off, these would be automatically set by use of the cassette ordered. Further, such setup of operating parameters may describe generally accepted setup for a specific surgical procedure.

The program memory of a pump can be updated with data forwarded with the data on the tag. In this respect, the pump can change operating mode and parameter from being an arthroscopy system to a urology system, for instance. This would mean that the pump could change most of its operating parameters, menu selections, user settable limits and sensitivity for optical detection of blood and debris, etc. This function can further be a small software update of the pump in general. In this respect it has to be noted that the data volume is very small on the RFID tags compared to the program memory of the system.

Specific data on patient group and surgical procedure can also be entered in the identification device. This includes specific calibration values for e.g. optical cavity and pressure calibration data values. RFID tag data may carry setup values for ACL (anterior cruciate ligament) surgery, small joint surgical procedures or TUR (Trans Uretheral Resection) in urology operations. Flow calibration values for the sterile product are also valuable data that can be entered by a test station at the production line The RFID technology may incorporate a passive tag without processor for encryption. This is powered by an electromagnetic field. An active RFID tag has its own power source, and does not have analytical capacity of encryption or similar functions. Both active or passive tags may however hold an encrypted serial number and both have the possibility to store information that is not, or is in part, possible to change by use of medical equipment.

The type of data stored in the information carrier is programmed during or after manufacture of the hose or cassette. The reading element is controlled by standard software FIGS. 1-8 are shown in the parent application, which are somewhat identical in appearance to the invention herein, but that the current invention is also an improvement in for example that an object of the invention herein is to make sure that technical data related to operation of equipment can be forwarded from the manufacturer to the distributed equipments through the use of the information carrier on the hose or cassette. This data includes operation modes, calibration factors, leasing or service expiration date, as well as data related to specific patient groups, surgical procedure, final user preferred operation settings, etc.

FIG. 1 is a schematic illustration of an infusion pump 1 that includes a pump hose-connecting device in accordance with the invention. The pump 1 also includes an impeller 2, which, in turn, includes two press wheels 3 which are intended to press a hose 4 against an arrestor 5 located in the pump. The hose part 4 is fitted to the pump 1 in the following manner: The arrestor 5 is raised about its mounting shaft 6, wherewith the impeller 2 acts as a bending means around which the part 4 of the hose is placed. One end of the hose part 4 is herewith fastened to the medical equipment (the infusion pump 1), in a conventional manner. The hose part 4 is then tensioned around the impeller 2 and stretched elastically into a position beneath a fixation seat 7 and fastened in this position. The seat 7 is fixedly connected to the pump 1. A holder 8 is fixedly connected to the hose part 4 in the region of the fixation seat 7, the holder being provided with an information carrier 9. In the case of the illustrated embodiment the holder 8 has the form of an alignment block that includes an upper oblique surface 10, which conforms to a corresponding oblique surface in the seat 7. The holder 8 is shown mounted in the seat 7 in the Figure, with the information carrier on the holder located opposite a reading element 12 disposed in the seat 7. As will be seen from the Figure, the reading element 12 is connected to a registering unit 13, which in turn, is connected to a storage unit 14 on the one hand and to an analyzing unit 15 on the other hand. The storage unit is also connected directly to the analyzing unit. A presentation unit 16 is connected directly to both the analyzing unit 15 and the storage unit 14. Depending on the nature of the information delivered from the information carrier 9 and checked in the analyzing unit 15, a control unit (not shown) as for example in US US2007249993, is actuated to either approve the connection of the hose part 4 to the equipment or to stop continued functioning of the pump 1.

FIGS. 2a and 2b are sectional views taken on the line A-A in FIG. 1, FIG. 2a illustrating a first embodiment and FIG. 2b a second embodiment. The embodiment according to FIG. 2a includes a holder 8 which is actively mounted in the seat 7 by virtue of its upper edge surface 21a being in abutment with a corresponding edge surface in the seat 7. In this case, the edge surface 21a is horizontally disposed, i.e. at right angles to the symmetry axis of the hose part 4, wherewith a pulling force applied upwardly to the hose part 4 in the Figure will bring the holder into alignment in the direction of the X and Y axes respectively in accordance with the coordinate system shown in FIG. 2a. This alignment of the holder in the X and Y directions respectively results in the alignment of the information carrier 9 in the holder 8 in two mutually perpendicular directions relative to the reading element 12.

FIG. 2b illustrates a second embodiment of a holder, 81, fitted in a fixation seat 71. In this embodiment the upper edge surface 21b, of the holder 81 is inclined inwardly of the seat 71 so that a pulling force applied upwardly on the hose part 4 in the Figure will result in the alignment of holder 81 also in the Z-direction in accordance with the coordinate system shown in FIG. 2a. This embodiment thus provides alignment of the information carrier 9 in all three mutually perpendicular directions X, Y and Z.

FIGS. 3a-3c illustrate a sequence of events in fitting the holder 8 applied to the hose part 4 in the fixation seat 7. After having secured the equipment-fixed end of the hose part 4 in the infusion pump, the hose part 4 is drawn over the impeller 2, wherewith the arrestor 5 snaps down and locks in the position shown in FIG. 1. The hose part 4 is then stretched down in FIG. 3, wherewith the holder 8 reaches a position in which it can be snapped into the seat 7, in accordance with the arrows in FIG. 3a.

FIG. 3b shows a state in which the hose part 4 has been brought closer in towards the seat 7. It will be seen that respective slide surfaces 10 and 11 in the holder 8 and the seat 7 are so angled in relation to each as to bring the information carrier 9 and the reading element 12 into alignment with one another.

FIG. 3c shows the device in its finally assembled state, although a small gap has been left around the holder 8 so that the positions of the surfaces 10, 11 and the information carrier 9 and the reading element 12 can be seen clearly. The Figure also shows the orthogonal coordinate system illustrated in FIG. 2a.

FIG. 4 is a sectional view of the identification device taken on the line B-B in FIG. 1. It will be seen that the hose part 4 is firmly fixed in the holder 8 and that an information carrier 9 is inserted into the holder. It will also be seen that the holder is fitted in the seat 7 and that the information carrier 9 is situated opposite the reading element 12, which is also inserted into the seat 7.

FIG. 5 is a sectional view taken on the line C-C in FIG. 1. As will evident from the Figure, the end of the hose part 4 is inserted into the seat 7 through an open slot 51 provided on one side thereof.

FIG. 6 shows another medical application for identifying a sterile product. This application relates to the use of an orthopaedic oscillating saw 60 to which there has been connected a sterile saw blade 62 that carries an information carrier 63. The information carrier 63 is located opposite a reading element 64 when the saw blade 62 has been fitted, the information carrier 63 and the reading element 64 being adapted to operate in a manner corresponding to that earlier described.

FIG. 7 illustrates a further application of the present invention. This application is concerned with the handgrip 70 of an orthopaedic drill to which there is fitted a sterile drill bit 72 that carries an information carrier 73. As in the earlier case, the information carrier 73 is also adapted to deliver or to offer specific product information to a reading element 74 connected to the handgrip 70.

A further embodiment is shown in FIG. 8. In this embodiment a shaver handgrip 80 has fitted thereto a sterile shaver blade 82 which, similar to the embodiments described in the foregoing, includes an information carrier 83 which, when the shaver blade 82 is fitted, is located opposite a reading element 84.

A newly disclosed embodiment is shown in FIG. 9. This embodiment is very similar to the one shown in FIG. 1 but in this case the hose part 4 is fixedly connected to a cassette part 17, being provided with an information carrier 9, located opposite to the reading element 12 on the equipment.

Figure 10A:
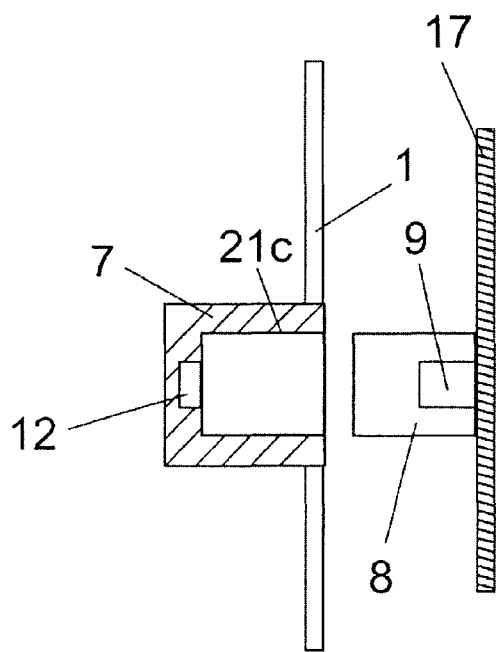
FIG. 10*a-b* illustrates still an. other embodiment of a device with a hose in combination with a cassette design.
Figure 10B:
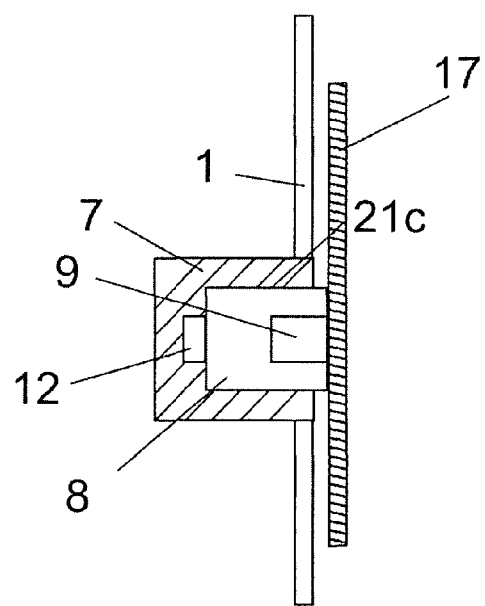

Still another embodiment is described in FIGS. 10a and 10b, which are sectional views of the identification device. Here it will be seen that a cassette part 17 is firmly fixed to the holder 8. An information carrier 9 is situated in the holder. It will also be seen that the holder is mounted in the fixation seat 7 and that the information carrier 9 is situated opposite the reading element 12, which is firmly fixed in the fixation seat 7.

FIGS. 10a-10b illustrates the sequence of events taking place when the holder 8 comprising the firmly fixed cassette part 17 is fitted or mounted in the fixation seat 7. The surface 21c is in abutment with a corresponding edge surface in the seat 7. FIG. 10a shows how the holder 8 is firstly moved towards the fixation seat 7, and thereafter placed as depicted in FIG. 10b.

As shown in the figures only a single mounting step is required for bringing the information carrier 9 situated in the holder 8 and the reading element 12 in the fixation seat 7 into contactless alignment with one another for enabling identification of the sterile product and transfer of information to the medical equipment for re-programming its operation.

Although the following description is concentrated on a hose and/or a cassette as the product and on an infusion pump as medical equipment, it will be understood that the present invention is particularly suitable with regard to other products and other pieces of equipment within the medical-technical field where high safety requirements with regard to sterility prevail.

Furthermore, it will be understood that other embodiments within the medical-technical field are conceivable within the scope of the invention, where transference of data from an information device to a medical equipment allows re-programming of the medical equipment so that it can operate in different modes, with different patient groups, surgical procedures or according to pre-selected criteria.

What is claimed is:

1. A medical identification device for use with medical equipment and for identifying a sterile product, the medical equipment including a reading element, the medical identification device including software for controlling operation of the medical equipment and programming the medical equipment such that its function and operation mode is changed, the medical identification device comprising:
    an information carrier mounted on the sterile product, the information carrier including specific information relating to the sterile product and the medical equipment,
    the information carrier configured to transfer the specific information in a contactless fashion to the reading element of the medical equipment when the sterile product is connected to the medical equipment,
    wherein the specific information is configured to alter the memory content of the medical equipment and control operation of the medical equipment independent of the features of the attached sterile device by changing at least one of a calibration factor, operating parameters depending on a user of the medical device, an operating mode, menu selections, user settable limits, or sensitivity for optical detection of blood and debris.

2. The identification device according to claim 1, wherein the information carrier is mounted in or on one side of a holder on the sterile product and the reading element is mounted in or on one side of a fixation seat in which the holder can be seated, wherein the exchange of information between the information carrier and the reading element does not take place until the holder is in place in the seat and until connection of the sterile product to the medical equipment has been completed.

3. The identification device according to claim 2, wherein the information carrier and the reading element are configured to take fixed positions relative to one another when the sterile product is connected actively to the medical equipment.

4. The identification device according to claim 1, wherein the transmission of information between the information carrier and the reading element is caused to take place with the aid of one or more device(s) selected from the group consisting of bar codes, Blue Tooth, radio waves, light waves including infrared light, electromagnetism, radioactivity and chemical transmission.

5. The identification device of claim 1, further comprising a registering unit connected to the reading element, and connected both to a storage unit and an analyzing unit.

6. The identification device of claim 5, wherein the information carrier further comprises a presentation unit which functions to present information from both the analyzing unit and the storage unit.

7. The identification device of claim 5, further comprising a programming unit connected to the analyzing unit or the storage unit for updating software controlling operation of the piece of medical equipment.

8. The identification device according to claim 1, wherein the specific information includes information relating to at least one of operation modes, calibration factors, leasing or service expiration, specific patient groups, surgical procedures, and final user preferred operation settings.

9. The identification device of claim 1, wherein the specific information is configured to alter the memory content of the medical equipment and control operation of the medical equipment independent of the features of the attached sterile device by changing at least one of the operating parameters depending on the user of the medical device or the operating mode of the medical equipment.

10. The identification device of claim 1, wherein the specific information is configured to alter the memory content of the medical equipment and control operation of the medical equipment independent of the features of the attached sterile device by changing the operating mode of the medical equipment.

11. The identification device of claim 10, wherein changing the operating mode of the medical equipment sets the medical equipment in at least one of a service mode, a demo mode, or a user operation mode.

12. The identification device of claim 10, wherein changing the operating mode of the medical equipment causes the medical equipment to operate either as an arthroscopy system or a urology system.

13. The identification device of claim 1, wherein the specific information is configured to alter the memory content of the medical equipment and control operation of the medical equipment independent of the features of the attached sterile device by changing the operating parameters depending on the user of the medical device.

14. A method for re-programming operation of medical equipment when the medical equipment is connected to a medical identification device, the method comprising the steps of:
    a) providing the medical identification device comprising an information carrier mounted to a sterile product, the information carrier configured to deliver specific information on the sterile product and the medical equipment in a contactless fashion to a reading element connected to the medical equipment;
    b) bringing the information carrier and the reading element into contactless alignment with one another for transfer of the specific information to the piece of medical equipment; and
    c) based on the transferred specific information, altering the memory content of the medical equipment and controlling operation of the medical equipment independent of the features of the attached sterile device by changing at least one of a calibration factor, operating parameters depending on a user of the medical device, an operating mode, menu selections, user settable limits, or sensitivity for optical detection of blood and debris.

15. The method of claim 14, wherein the memory content of the medical equipment is altered and the operation of the medical equipment is controlled independent of the features of the attached sterile device by changing at least one of the operating parameters depending on the user of the medical device or the operating mode.

16. The method of claim 14, wherein the memory content of the medical equipment is altered and the operation of the medical equipment is controlled independent of the features of the attached sterile device by changing the operating mode of the medical equipment.

17. The method of claim 16, wherein changing the operating mode of the medical equipment sets the medical equipment in at least one of a service mode, a demo mode, or a user operation mode.

18. The method of claim 16, wherein changing the operating mode of the medical equipment causes the medical equipment to operate either as an arthroscopy system or a urology system.

19. The method of claim 14, wherein the memory content of the medical equipment is altered and the operation of the medical equipment is controlled independent of the features of the attached sterile device by changing the operating parameters depending on the user of the medical device.

* * * * *